US012721582B2

(12) United States Patent
Zhang et al.

(10) Patent No.: US 12,721,582 B2
(45) Date of Patent: Sep. 1, 2026

(54) MAMMOGRAPHY SYSTEM AND IMAGING METHOD

(71) Applicant: Shanghai United Imaging Healthcare Co., Ltd., Shanghai (CN)

(72) Inventors: Yu Zhang, Shanghai (CN); Juan Feng, Shanghai (CN); Jie Niu, Shanghai (CN)

(73) Assignee: Shanghai United Imaging Healthcare Co., Ltd., Shanghai (CN)

(*) Notice: Subject to any disclaimer, the term of this patent is extended or adjusted under 35 U.S.C. 154(b) by 158 days.

(21) Appl. No.: 18/814,574

(22) Filed: Aug. 25, 2024

(65) Prior Publication Data

US 2025/0064418 A1 Feb. 27, 2025

(30) Foreign Application Priority Data

Aug. 24, 2023 (CN) ........................ 202311079588.X

(51) Int. Cl.

| | |
|---|---|
| ***A61B 6/50*** | (2024.01) |
| ***A61B 6/00*** | (2006.01) |
| ***A61B 6/58*** | (2024.01) |

(52) U.S. Cl.

CPC .............. *A61B 6/502* (2013.01); *A61B 6/483* (2013.01); *A61B 6/583* (2013.01)

(58) Field of Classification Search

CPC .......... A61B 6/502; A61B 6/483; A61B 6/583

See application file for complete search history.

(56) References Cited

U.S. PATENT DOCUMENTS

| | | | | |
|---|---|---|---|---|
| 2003/0072409 A1* | 4/2003 | Kaufhold | ............... | A61B 6/502 378/53 |
| 2010/0321404 A1* | 12/2010 | Fischer | .................. | G16Z 99/00 345/632 |

FOREIGN PATENT DOCUMENTS

| | | | |
|---|---|---|---|
| CN | 101382505 | A | 3/2009 |
| CN | 103445795 | A | 12/2013 |
| CN | 104367331 | B | 2/2017 |
| CN | 107802280 | A | 3/2018 |
| CN | 108335269 | A | 7/2018 |
| CN | 108765421 | A | 11/2018 |
| CN | 110840469 | A | 2/2020 |
| CN | 111028310 | A | 4/2020 |
| DE | 102010034680 | A1 | 3/2012 |

* cited by examiner

*Primary Examiner* — Hugh Maupin

(57) ABSTRACT

A mammography system and a method for imaging at least part of a breast with the mammography system are disclosed. The method includes: obtaining pre-exposure images respectively corresponding to a plurality of phantoms by performing pre-exposure for each of the plurality of phantoms with a respective predetermined dosage, each phantom having its respective compression thickness and component composition; determining a relationship among a target grayscale, the compression thickness and the component composition by performing de-scattering processing on each pre-exposure image based on the compression thickness and the component composition of the phantom corresponding to the pre-exposure image; determining a target dosage for a target breast based on a compression thickness and a component composition of the target breast, and the relationship; and acquiring a main exposure image by performing exposure for the target breast based on the target dosage.

20 Claims, 6 Drawing Sheets

S802

Determine a second scatter kernel corresponding to the target breast, based on the compression thickness and the component composition of the target breast

S804

Perform de-scattering iterative processing on the main exposure image, based on the second scatter kernel

MAMMOGRAPHY SYSTEM AND IMAGING METHOD

CROSS-REFERENCE TO RELATED APPLICATIONS

The present application claims priority to Chinese patent application No. 202311079588.X, filed on Aug. 24, 2023, the entire content of which is incorporated herein by reference.

TECHNICAL FIELD

The present disclosure relates to the field of medical imaging, and in particular, to a mammography system and a method for imaging at least part of a breast with a mammography system.

BACKGROUND

Compton scattering occurs in the process of irradiating and penetrating the object to be imaged by X-rays from the mammography system, so that scattered X-rays are generated and received by a detector of the mammography system, forming an effective grayscale contribution. In fact, this part of the ray is useless information, and this kind of ray passes through the human body and irradiates disorderly on the detector, thus it is the reaction contribution to the primary beam. As a result, it is desirable to eliminate the effect of scattered X-rays on imaging.

In most conventional mammography systems, one-dimensional or two-dimensional anti-scatter grids are used to filter out the scattering component, leaving the useful main radiation components for subsequent image algorithm analysis, and subsequent image post-processing operations.

SUMMARY

In conventional mammography systems which apply energy-integrating detectors, the use of the anti-scatter grids has a disadvantage that the attenuation by the anti-scatter grids in the process of achieving the same grayscale increases the absorption dosage of the patient. The increased dosage is the excess dosage of the patient which is superfluously irradiated.

The present disclosure provides a mammography system and a method for imaging at least part of a breast with a mammography system, which can remove scatter in a mammographic image without using any anti-scatter grid.

A first aspect of the present disclosure provides a method for imaging at least part of a breast with a mammography system. The method includes: obtaining pre-exposure images respectively corresponding to a plurality of phantoms by performing pre-exposure for each of the plurality of phantoms with a respective predetermined dosage, each phantom having its respective compression thickness and component composition; determining a relationship among a target grayscale, the compression thickness and the component composition by performing de-scattering processing on each pre-exposure image based on the compression thickness and the component composition of the phantom corresponding to the pre-exposure image; determining a target dosage for a target breast based on a compression thickness and a component composition of the target breast, and the relationship; and acquiring a main exposure image by performing exposure for the target breast based on the target dosage.

In the first aspect, performing de-scattering processing on each pre-exposure image based on the compression thickness and the component composition of the phantom corresponding to the pre-exposure image includes: determining a first scatter kernel corresponding to the phantom, based on the compression thickness and the component composition of the phantom; and performing de-scattering iterative processing on the pre-exposure image, based on the first scatter kernel corresponding to the phantom.

In the first aspect, performing de-scattering iterative processing on the pre-exposure image, based on the first scatter kernel corresponding to the phantom, includes: obtaining a scattering image corresponding to the pre-exposure image by performing a convolution operation on the pre-exposure image and the first scatter kernel; obtaining a primary beam image corresponding to the phantom, based on the pre-exposure image and the scattering image; and updating the first scatter kernel based on a determination that the primary beam image fails to satisfy a convergence condition, until the primary beam image satisfies the convergence condition.

In the first aspect, obtaining a primary beam image corresponding to the phantom, based on the pre-exposure image and the scattering image, includes: subtracting the scattering image from the pre-exposure image to obtain the primary beam image corresponding to the phantom.

In the first aspect, the convergence condition is that an error between the obtained primary beam image and a measured primary beam image is less than a predetermined error threshold.

In the first aspect, determining the target dosage for the target breast based on the compression thickness and the component composition of the target breast, and the relationship, includes: determining a target grayscale corresponding to the target breast, based on the compression thickness and the component composition of the target breast, and the relationship; and determining the target dosage based on the target grayscale.

In the first aspect, acquiring the main exposure image by performing exposure for the target breast based on the target dosage, includes: determining an exposure parameter based on the target dosage; and performing the exposure for the target breast based on the exposure parameter, to obtain the main exposure image.

In the first aspect, the method further includes: determining a second scatter kernel corresponding to the target breast, based on the compression thickness and the component composition of the target breast; and performing de-scattering iterative processing on the main exposure image, based on the second scatter kernel.

In the first aspect, the method further includes: denoising the main exposure image after the de-scattering iterative processing has been completed.

A second aspect of the present disclosure provides a mammography system. The mammography system includes a scanning device and a processing device. The scanning device is configured to: generate pre-exposure images respectively corresponding to a plurality of phantoms by performing pre-exposure for each of the plurality of phantoms with a respective predetermined dosage, each phantom having its respective compression thickness and component composition; and generate a main exposure image by performing exposure for a target breast based on a target dosage. The processing device is configured to: acquire the pre-exposure images from the scanning device; determine a relationship among a target grayscale, the compression thickness and the component composition by performing de-scattering processing on each pre-exposure image based on the compression thickness and the component composition of the phantom corresponding to the pre-exposure image; determine a target dosage for a target breast based on a compression thickness and a component composition of the target breast, and the relationship; and acquire the main exposure image from the scanning device.

In the second aspect, performing de-scattering processing on each pre-exposure image based on the compression thickness and the component composition of the phantom corresponding to the pre-exposure image includes: determining a first scatter kernel corresponding to the phantom, based on the compression thickness and the component composition of the phantom; and performing de-scattering iterative processing on the pre-exposure image, based on the first scatter kernel corresponding to the phantom.

In the second aspect, performing de-scattering iterative processing on the pre-exposure image, based on the first scatter kernel corresponding to the phantom, includes: obtaining a scattering image corresponding to the pre-exposure image by performing a convolution operation on the pre-exposure image and the first scatter kernel; obtaining a primary beam image corresponding to the phantom, based on the pre-exposure image and the scattering image; and updating the first scatter kernel based on a determination that the primary beam image fails to satisfy a convergence condition, until the primary beam image satisfies the convergence condition.

In the second aspect, determining the target dosage for the target breast based on the compression thickness and the component composition of the target breast, and the relationship, includes: determining a target grayscale corresponding to the target breast, based on the compression thickness and the component composition of the target breast, and the relationship; and determining the target dosage based on the target grayscale.

In the second aspect, the processing device is further configured to: determine an exposure parameter based on the target dosage; and transmit the exposure parameter to the scanning device.

In the second aspect, the processing device is further configured to: determining a second scatter kernel corresponding to the target breast, based on the compression thickness and the component composition of the target breast; and performing de-scattering iterative processing on the main exposure image, based on the second scatter kernel.

A third aspect of the present disclosure provides a method for imaging at least part of a breast with a mammography system. The method includes: obtaining a relationship among a target grayscale, a compression thickness, and a component composition; determining a target dosage for a target breast based on the relationship, a compression thickness of the target breast, and a component composition of the target breast; and performing exposure for the target breast based on the target dosage.

In the third aspect, the relationship is obtained by: obtaining pre-exposure images respectively corresponding to a plurality of phantoms by performing pre-exposure for each of the plurality of phantoms with a respective predetermined dosage, each phantom having its respective compression thickness and component composition; and determining the relationship among the target grayscale, the compression thickness and the component composition by performing de-scattering processing on each pre-exposure image based on the compression thickness and the component composition of the phantom corresponding to the pre-exposure image.

In the third aspect, the relationship is obtained via artificial intelligence (AI).

In the third aspect, performing de-scattering processing on each pre-exposure image based on the compression thickness and the component composition of the phantom corresponding to the pre-exposure image includes: determining a first scatter kernel corresponding to the phantom, based on the compression thickness and the component composition of the phantom; and performing de-scattering iterative processing on the pre-exposure image, based on the first scatter kernel corresponding to the phantom.

In the third aspect, performing de-scattering iterative processing on the pre-exposure image, based on the first scatter kernel corresponding to the phantom, includes: obtaining a scattering image corresponding to the pre-exposure image by performing a convolution operation on the pre-exposure image and the first scatter kernel; obtaining a primary beam image corresponding to the phantom, based on the pre-exposure image and the scattering image; and updating the first scatter kernel based on a determination that the primary beam image fails to satisfy a convergence condition, until the primary beam image satisfies the convergence condition.

A fourth aspect of the present disclosure provides a computer apparatus. The computer apparatus includes a processor and a memory storing a computer program. The computer program, when executed by the processor, causes the processor to implement the steps of the method in the first aspect or the third aspect.

In a fifth aspect of the present disclosure provides a non-volatile computer-readable storage medium. The computer program is configured to cause, when executed by a processor, the processor to implement the steps of the method in the first aspect or the third aspect.

BRIEF DESCRIPTION OF THE DRAWINGS

The accompanying drawings, which are incorporated, in and, constitute a part of the specification, illustrate one or more embodiments and, together with the description, explain these embodiments.

DETAILED DESCRIPTION OF THE EMBODIMENTS

Figure 1:
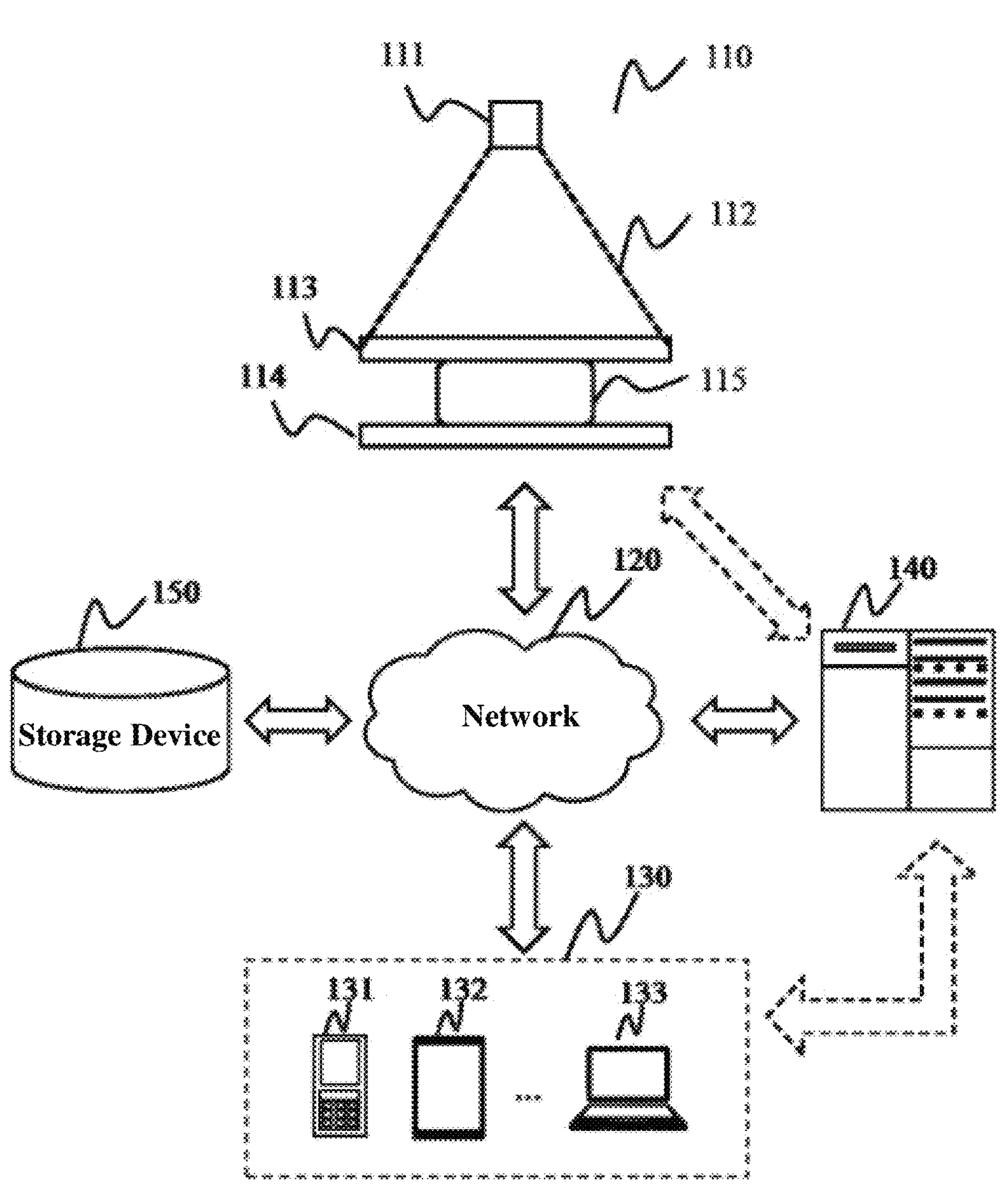
FIG. 1 is a schematic diagram illustrating a mammography system according to an embodiment of the present disclosure.

In order to make the above objectives, features and advantages of the present disclosure more apparent and understandable, specific implementations of the present disclosure are described in detail below with reference to the accompanying drawings. In the following description, many specific details are set forth in order to fully understand the present disclosure. However, the present disclosure can be implemented in many other ways different from those described herein, and those of ordinary skill in the art can make similar improvements without departing from the connotation of the present disclosure. Therefore, the present disclosure is not limited by the specific embodiments disclosed below.

In the present disclosure, unless otherwise clearly specified and limited, the terms "first" and "second" are used for descriptive purposes only, and cannot be interpreted as indicating or implying relative importance or implicitly specifying the quantity of indicated technical features. Thus, the features defined as "first" and "second" may explicitly or implicitly include at least one of these features. In the description of the present disclosure, "plurality" means at least two, such as two, three, etc., unless otherwise clearly and specifically defined.

Terminology used herein is for the purpose of describing particular embodiments only and is not intended to be limiting of the present disclosure. For example, as used herein, the singular forms "a", "an" and "the" are intended to include the plural forms as well, unless the context clearly indicates otherwise. It will be further understood that the terms "includes" and/or "including," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

It will be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments.

Although in the present disclosure, various references in the present disclosure are made to certain modules in the system according to the embodiments, however, any number of different modules can be used and run on a computing apparatus and/or a processor. The modules are illustrative only, and different modules can be used in different aspects of the system and the method.

FIG. 1 is a schematic diagram illustrating a mammography system according to an embodiment of the present disclosure, in which the mammography system is indicated by a reference numeral 100.

As shown in FIG. 1, the mammography system 100 may include a scanning device 110, a network 120, at least one terminal 130, a processing device 140, and a storage device 150. The scanning device 110, at least one terminal 130, the processing device 140, and/or the storage device 150 may be connected or communicated with each other by a wired connection, a wireless connection (e.g., the network 120), or any combination thereof. The connection between the members of the mammography system 100 may be variable. Just as an example, the scanning device 110 may be connected to the processing device 140 through the network 120, as shown in FIG. 1. For another example, the scanning device 110 may be directly connected to the processing device 140. For another example, the storage device 150 may be connected to the processing device 140 through the network 120, or the storage device 150 may be directly connected to the processing device 140, as shown in FIG. 1. As an example, the terminal 130 may be connected to the processing device 140 through the network 120, or the terminal 130 may be directly connected to the processing device 140, as shown in FIG. 1.

The scanning device 110 may include a ray source 111, a compression paddle 113, a detector 114, a motor (not illustrated), and a target breast 115. The ray source 111 may be fixed or moved (for example, left, right, upward, or downward) above the target breast 115 which is static and compressed. The ray source 111 may also be rotated around the static, compressed target breast 115. The ray source 111 is configured to emit rays 112, such as X-rays. The X-rays may include soft X-rays (e.g., molybdenum target X-rays of about 30 kV). The ray source 111 may have a target material selected from the group consisting of tungsten, molybdenum, copper, rhodium, silver, aluminum, and combinations thereof. The rays 112 (e.g., X-rays) emitted by the ray source 111 may be in a form of a pencil beam matrix.

The compression paddle 113 is configured to compress a target breast 115 to reduce the thickness of the target breast 115, so that the target breast 115 has more consistent thickness. After being compressed by the compression paddle 113, overlapping soft tissues in the target breast 115 can be separated, and the target breast 115 can be fixed to prevent image blur caused by the movement of the target breast 115. The smaller the thickness of the target breast 115, the less scatter radiation it produces, and the higher the contrast of the resulting image. Therefore, within the tolerance range (such as the tolerance to pain) of the subject, the greater the compression of the target breast 115, the better. Scatter is a phenomenon in which an X-ray interacts with electrons in an object to be imaged to change direction when passing through the object. Instead of propagating in a straight line, the scattered rays are scattered at different angles, some of which reach the detector. The presence of scattered rays reduces the contrast and resolution of the image because they contain unrelated information.

The detector 114 may include an X-ray detector, a photographic film, etc. In some embodiments, the X-ray detector may include a housing of the detector (not illustrated), an image receptor, etc.

The scanning device 110 may be operated as follows. The target breast 115 of the subject is placed above the housing of the detector 114 (not illustrated), a lower surface of the compression paddle 113 abuts against a top of the target breast 115, and the motor is started to cause the compression paddle 113 to slowly press downwards, until a certain compression state is reached. The certain compression state is related to the tolerance range (e.g., tolerance to pain) of the subject. The ray source 111 emits rays 112, and the rays penetrate the compression paddle 113, the compressed target breast 115 (i.e., the target breast 115 at a certain compression thickness), an air layer between the compression paddle 113 and the detector 114 (i.e., the air layer at a certain compression thickness), and/or the air layer between the housing (not illustrated) of the detector and the image receptor. Then the detector 114 detects the rays to form an image. In some embodiments, the ray source may be fixed or moved (for example, left, right, upward, or downward) above the compressed breast, or may be rotated around the compressed breast at for example −45°–45°, and at least one two-dimensional breast image can be directly acquired through the detector. In other embodiments, at least two two-dimensional breast images can be used to reconstruct a three-dimensional breast image.

The network 120 may include any suitable network that can facilitate information and/or data exchange in the mammography system 100. At least one component of the mammography system 100 (e.g., the scanning device 110, the processing device 140, the storage device 150, or the terminal 130) may exchange information and/or data with at least one other component of the mammography system 100 through the network 120. For example, the processing device 140 may acquire a breast image (e.g., a two-dimensional breast image) from the scanning device 110 through the network 120. For another example, the processing device 140 may acquire a user (e.g., a doctor) instruction from the terminal 130 through the network 120. The network 120 may include a public network (e.g., the Internet), a private network (e.g., a local area network (LAN)), a wired network, a wireless network (e.g., an 802.11 network, or a Wi-Fi network), a frame relay network, a virtual private network (VPN), a satellite network, a telephone network, a router, a hub, a switch, a server computer, and/or any combination thereof. For example, the network 120 may include a wired network, a wireless network, an optical fiber network, a telecommunication network, an intranet, a wireless local area network (WLAN), a metropolitan area network (MAN), a public switched telephone network (PSTN), a Bluetooth™ network, a ZigBee™ network, a near field communication (NFC) network, or any combination thereof. In some embodiments, the network 120 may include at least one network access point. For example, the network 120 may include a wired and/or wireless network access point, such as a base station and/or an Internet exchange point, and at least one component of the mammography system 100 may be connected to the network 120 through the access point to exchange data and/or information.

In some embodiments, a user (e.g., a doctor, etc.) can operate the mammography system 100 through the terminal 130. The terminal 130 may include at least one of a mobile device 131, a tablet computer 132, a laptop computer 133, or any combination thereof. The terminal 130 may include an input device, an output device, and the like. The input device may include alphabetic keys, numeric keys, and other keys, and the input device may optionally be a keyboard, a touch screen (e.g., with tactile or haptic feedback) input, a voice input, an eye-tracking input, a brain monitoring system, or any other similar input mechanism. Input information received by the input device may be transmitted to the processing device 140 via, for example, a bus for further processing. Other types of the input device may include a cursor control device, such as a mouse, a trackball, or cursor direction keys. The output device may include a display, a speaker, a printer, and the like, or any combination thereof. In some embodiments, the terminal 130 may include a part of the processing device 140.

Figure 9:
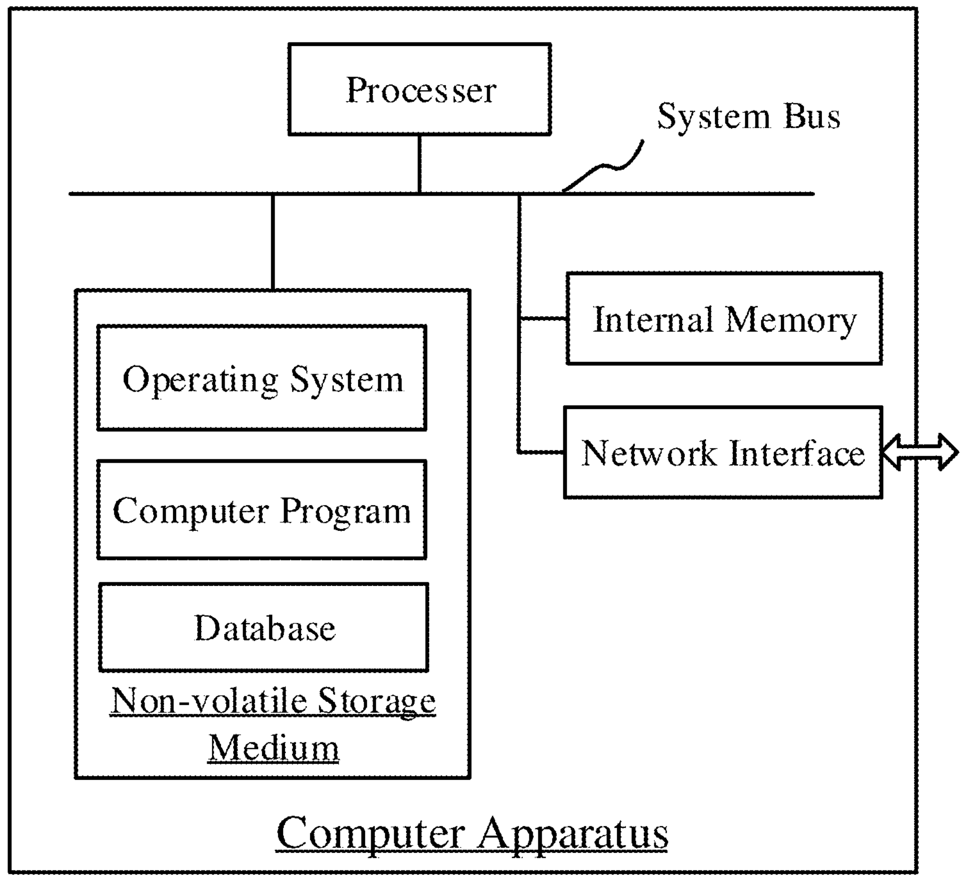
FIG. 9 is a schematic diagram illustrating a computer apparatus according to an embodiment of the present disclosure.

The processing device 140 may process data and/or information acquired from the scanning device 110, the storage device 150, the terminal 130, or other components of the mammography system 100. For example, the processing device 140 may perform de-scattering processing on the breast image (e.g., the two-dimensional breast image) generated by the scanning device 110. In some embodiments, the processing device 140 may include a single server or a server cluster consisting of a plurality of servers. The server cluster may be a centralized server cluster or a distributed server cluster. In some embodiments, the processing device 140 may access information and/or data from the scanning device 110, the storage device 150, and/or the terminal 130 through the network 120. For another example, the processing device 140 may be directly connected to the scanning device 110, the terminal 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, a cloud between clouds, a multi-layer cloud, etc., or any combination thereof. In some embodiments, the processing device 140 may be implemented as a computer apparatus 200 (as shown in FIG. 9) having one or more components.

The storage device 150 may store data, instructions, and/or any other information. In some embodiments, the storage device 150 may store prior data. The prior data includes parameters of the mammography system 100 and data on a first scatter kernel. The storage device 150 may store data (e.g., compression thickness) acquired from the scanning device 110, the terminal 130, and/or the processing device 140. In some embodiments, the storage device 150 may store data and/or instructions used by the processing device 140 to execute or use to complete the exemplary methods described in the present disclosure. In some embodiments, the storage device 150 may include a large-capacity memory, a removable memory, a volatile read-write memory, a read-only memory (ROM), or any combination thereof. An exemplary large-capacity memory may include a magnetic disk, an optical disk, a solid-state disk, etc. An exemplary removable memory may include a flash drive, a floppy disk, an optical disk, a memory card, a compressed disk, a tape, etc. An exemplary volatile read-write memory may include random access memory (RAM). An exemplary RAM may include a dynamic random access memory (DRAM), a double data rate synchronous dynamic random access memory (DDRSDRAM), a static random access memory (SRAM), a thyristor random access memory (T-RAM), and a zero capacitance random access memory (Z-RAM), etc. An exemplary read-only memory may include mask read-only memories (MROMs), programmable read-only memories (PROMs), erasable programmable read-only memories (PEROMs), electrically erasable programmable read-only memories (EEPROMs), compact disk read-only memories (CD-ROMs), and a digital versatile disk read-only memory, etc. In some embodiments, the storage device 150 may be implemented on a cloud platform, as described elsewhere in the present disclosure.

In some embodiments, the storage device 150 may be connected to the network 120 to communicate with at least one other component in the mammography system 100 (e.g., the processing device 140, or the terminal 130). At least one component in the mammography system 100 may access data or instructions in the storage device 150 through the network 120. In some embodiments, the storage device 150 may include a part of the processing device 140.

It should be noted that the above is provided for illustrative purposes only and is not intended to limit the scope of the present disclosure. For those of ordinary skill in the art, under the guidance of the content of the present disclosure, various changes and modifications can be made. The features, structures, methods, and other features of the exemplary embodiments described in the present disclosure can be combined in various ways to obtain additional and/or alternative exemplary embodiments.

Figures 2, 3:
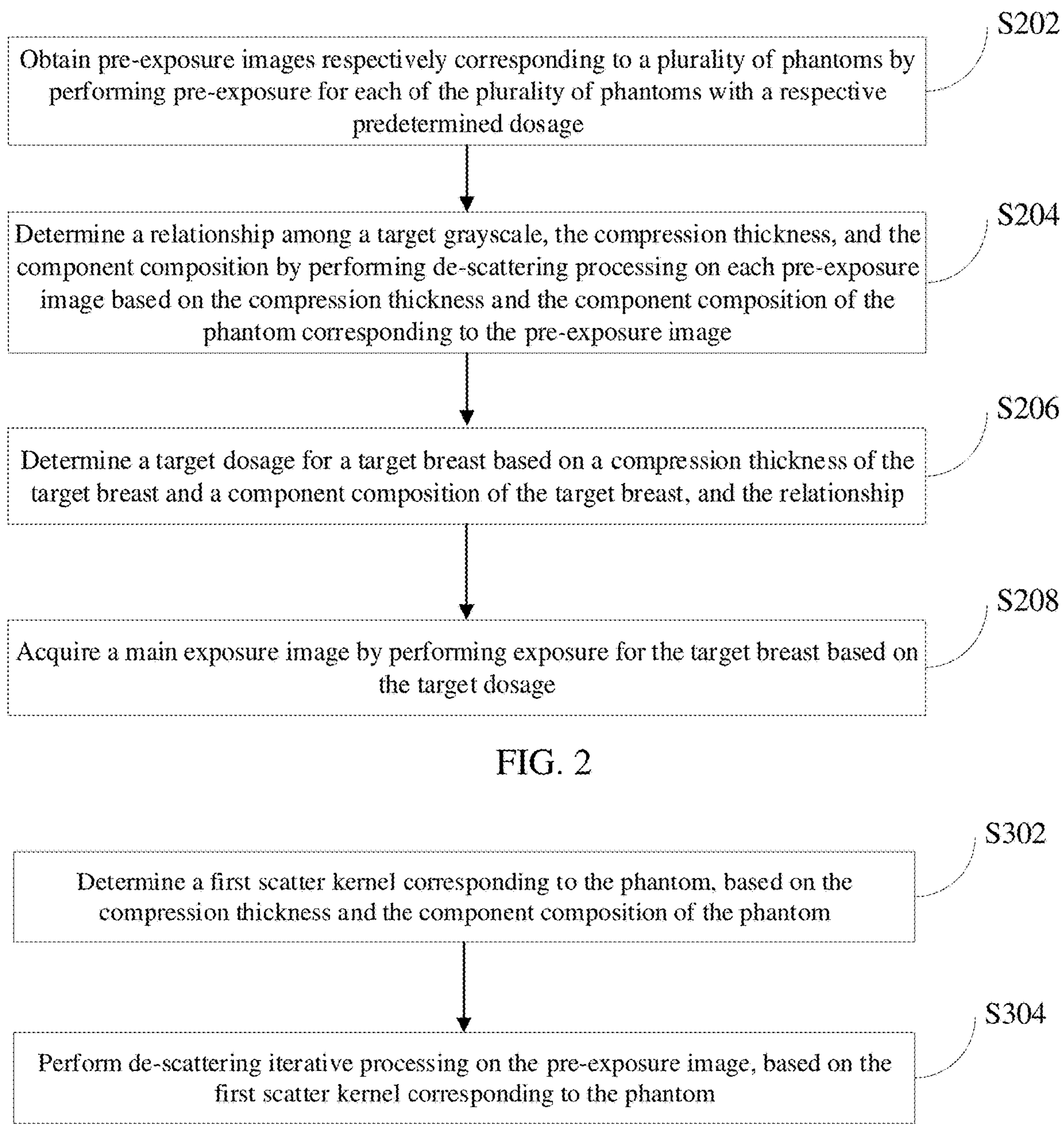
FIG. 2 is a flow diagram illustrating a method for imaging at least part of a breast with a mammography system according to an embodiment of the present disclosure.
FIG. 3 is a flow diagram illustrating a process of removing scatter in a pre-exposure image according to an embodiment of the present disclosure.

FIG. 2 is a flow diagram illustrating a method according to an embodiment of the present disclosure. The method can remove scattering component in a mammographic image without using any anti-scatter grid. As shown in FIG. 2, the method includes steps S202 to S208.

In step S202, pre-exposure images respectively corresponding to a plurality of phantoms are obtained by performing pre-exposure for each of the plurality of phantoms with a respective predetermined dosage.

The pre-exposure is an exposure process for acquire imaging data for the phantom. The phantom mentioned herein may also be referred to as a mammary phantom, which is an equivalent phantom of the mammary gland. The phantoms are used to simulate breasts of different component compositions for a human body. Each phantom has its respective compression thickness and component composition. The component of the breast may include at least glandular tissue and adipose tissue. The proportion of the glandular tissue is positively correlated with the scattering generated by the phantom. The larger the proportion of the glandular tissue, the larger the scattering generated by the phantom is. The compression thickness is a distance between the compression paddle and the detector after the target breast (or the phantom during the pre-exposure) is compressed by the compression paddle.

For the human body, the compression thickness ranges from 1 cm to 20 cm, and the proportion of the glandular tissue to the component of the breast ranges from 0 to 100%. The phantoms of different component compositions and different compression thicknesses may be formed by combining the glandular tissue and the adipose tissue. For example, a plurality of glandular blocks may be used to represent a plurality of predetermined amounts of glandular tissue respectively, and a plurality of adipose blocks may be used to represent a plurality of predetermined amounts of adipose tissue respectively, the glandular blocks and the adipose blocks have the same cross-sectional area but different thicknesses, and the phantoms may be constructed by different combinations of the glandular blocks and the adipose blocks. The pre-exposure image may be, for example, a two-dimensional breast image, or a three-dimensional breast image.

A plurality of predetermined dosages are determined in advance for the plurality of phantoms, respectively. That is, each phantom is pre-exposed with its respective predetermined dosage. For mammography, there is a requirement in regulatory standards to absorption dose for each compression thickness. Different absorption doses react directly on the grayscale of the image generated by the detector. In this embodiment, for each of the plurality of phantoms having its respective compression thickness and component composition, the predetermined dosage is determined in such a way that the pre-exposure image of the phantom has a desired grayscale, which is used as a target grayscale as described below. Different phantoms having different compression thickness may be pre-exposed with different predetermined dosages. For example, if a first phantom has a first compression thickness, and a second phantom has a second compression thickness different from the first compression thickness, the first phantom may be pre-exposed with a first predetermined dosage, and the second phantom may be pre-exposed with a second predetermined dosage. Different phantoms having the same compression thickness but different component compositions may be pre-exposed with the same predetermined dosage. For example, if a third phantom has the same compression thickness as a fourth phantom, but the third and fourth phantoms have different component compositions, the third and fourth phantoms may be pre-exposed with the same predetermined dosage. Since the component compositions of the third and fourth phantoms are different, the pre-exposure image of the third phantom has a grayscale different from the pre-exposure image of the fourth phantom. According to the different component compositions of the phantoms, the scattering components can be estimated, and a relationship among the grayscale (i.e., the target grayscale), the compression thickness, and the component can be determined. The process of determining the relationship is described as below.

The following table exemplarily shows the grayscales of pre-exposure images obtained after pre-exposure of each of the plurality of phantoms with the predetermined dosage. The grayscale is hereafter referred to as the target grayscale, which is the grayscale of the main exposure image to be realized.

TABLE 1

| Compression Thickness (mm) | Proportion of Glandular Tissue (%) | Target Grayscale |
|---|---|---|
| 10 | 0 | 400 |
| 10 | 20 | 380 |
| 10 | 50 | 360 |
| 10 | 80 | 340 |
| 10 | 100 | 320 |
| 20 | 0 | 300 |
| 20 | 20 | 280 |
| 20 | 50 | 260 |
| 20 | 80 | 240 |
| 20 | 100 | 220 |
| | . . . | |
| 90 | 0 | 100 |
| 90 | 20 | 90 |
| 90 | 50 | 80 |
| 90 | 80 | 70 |
| 90 | 100 | 60 |

In the above table, the component composition of the phantom is represented by the proportion of the glandular tissue. As will be described below, the component of the breast may include at least glandular tissue and adipose tissue. If the proportion of the glandular tissue is 0%, it means the phantom corresponds to a breast consists substantially of adipose tissue. If the proportion of the glandular tissue is 100%, it means the phantom corresponds to a breast consists substantially of glandular tissue. The above table shows that if different phantoms having the same compression thickness but different component compositions are pre-exposed with the same predetermined dosage, the higher the proportion of the glandular tissue, the smaller the grayscale of the pre-exposure image. This is because the larger the proportion of the glandular tissue, the larger the scattering generated by the phantom is.

In step S204, a relationship among a target grayscale, the compression thickness and the component composition is determined by performing de-scattering processing on each pre-exposure image based on the compression thickness and the component composition of the phantom corresponding to the pre-exposure image.

After the de-scattering processing, the complete primary beam component can be left in the pre-exposure image. It can be understood that the scattering component of the pre-exposure image is related to the compression thickness and the component composition of the phantom. Therefore, in this embodiment, the de-scattering process is performed on each pre-exposure image based on the compression thickness and the component composition of the phantom. The grayscale (that is, the target grayscale) on the pre-exposure image after the de-scattering processing exhibits the optical absorption distribution of the phantom to the X-ray, and in the case of radiating the X-ray with the predetermined dosage, the grayscale is associated with the compression thickness and the component composition of the phantom.

In step S206, a target dosage for a target breast is determined, based on a compression thickness and a component composition of the target breast, and the relationship.

In step S208, a main exposure image is acquired by performing exposure for the target breast based on the target dosage.

The main exposure is an acquisition process for acquire imaging data for the target breast. The main exposure image has the target grayscale.

Based on the above steps S202 to S208, in a pre-exposure stage, the de-scattering processing is performed on pre-exposure images corresponding to the phantoms to determine the relationship among the target grayscale, the compression thickness and the component composition. In a main exposure stage, the target dosage is determined based on the compression thickness and the component composition of the target breast, and the relationship, and the main exposure is performed for the target breast based on the target dosage, to obtain the main exposure image. In this embodiment, the target dosage can be determined more accurately, and scatter in the mammographic image can be removed without using any anti-scatter grid. Compared with a conventional de-scattering method of using the anti-scatter grid, the target dosage applied in this embodiment is lower.

In addition, since the scatter in the mammographic image can be removed without using any anti-scatter grid in this embodiment, that is, the anti-scatter grid and its respective moving grid mechanism are removed in the system, miniaturization of the mammography system can be further achieved and the cost of the mammography system can be reduced. The method in this embodiment can improve the controllability of the mammography system compared with the conventional de-scattering method of using the anti-scatter grid in which the processing accuracy of the anti-scatter grids is relatively high, and the difference in the uniformity of the anti-scatter grids affects the controllability of imaging.

Further, the method according to the present embodiment can be combined with breast magnification mammography, contact mode photography, tomosynthesis photography, multi-device fusion photography, graceless photography for a DR device, and graceless photography for a small C-arm, and has a wide range of application prospects.

As shown in FIG. 3, the step S202 of performing de-scattering processing on each pre-exposure image based on the compression thickness and the component composition of the phantom corresponding to the pre-exposure image includes the following steps S302 and S304.

In step S302, a first scatter kernel corresponding to the phantom is determined based on the compression thickness and the component composition of the phantom.

It can be understood that the first scatter kernel of the phantom is related to the compression thickness and the component composition of the phantom. Thus, the first scatter kernel corresponding to the phantom can be determined based on the compression thickness and the component composition of each phantom. A set of scatter kernels (i.e., a first scatter kernel) can be generated in advance for the phantoms by simulation experiments, which are associated with the thickness of the phantom (that is, compression thickness), the distance between the phantom and the detector, and the material of the phantom. In the case where the thickness, the distance and the material are known, it is possible to generate a scatter kernel required to reach a predetermined scattering distribution. The scatter kernel represents a probability distribution function of first scattering of X-rays as they pass through the phantom. The scatter kernel may be generated by for example, a Monte Carlo method using a Monte Carlo simulation software, deconvolution calculation or Taylor expansion, or generated based on for example, measurements from a plurality of detectors, or other known ways, which have the same basic principles and are not described herein.

In step S304, de-scattering processing is performed on the pre-exposure image, based on the first scatter kernel corresponding to the phantom. For example, the de-scattering processing includes iterative processing.

Exemplarily, in this embodiment, a Monte Carlo algorithm is used to process the pre-exposure image based on the first scatter kernel, thereby implementing de-scattering iterative processing on the pre-exposure image.

Figure 4:
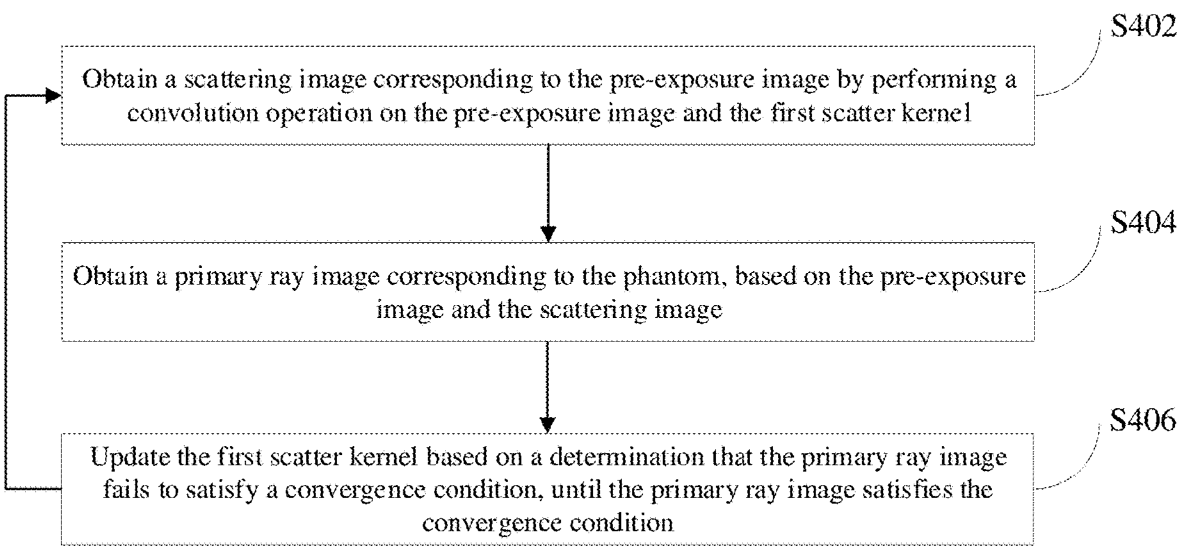
FIG. 4 is a flow diagram illustrating another process of removing scatter in a pre-exposure image according to an embodiment of the present disclosure.

As shown in FIG. 4, the step S304 of performing de-scattering iterative processing on the pre-exposure image based on the first scatter kernel corresponding to the phantom includes the following steps S402 and S404.

In step S402, a scattering image corresponding to the pre-exposure image is obtained by performing a convolution operation on the pre-exposure image and the first scatter kernel.

In this embodiment, the pre-exposure image is a 2D image, and the scattering image corresponding to the pre-exposure image can be obtained by performing the convolution operation on the pre-exposure image and the first scatter kernel. In other embodiments, the pre-exposure image may be a 3D image. In this case, the scattering image corresponding to the pre-exposure image can be obtained by a back projection algorithm based on the pre-exposure image and the first scatter kernel.

In step S404, a primary beam image corresponding to the phantom is obtained based on the pre-exposure image and the scattering image. The primary beam image means a filtered image having substantially only the primary beam component, which is obtained by filtering the scattering component from the pre-exposure image. The primary beam component means the X-ray emitted by the X-ray source and passed directly through the object to be imaged to the detector, which are not subjected to any scattering events and thus retain the original information after passing through the object. The primary beam component carries useful information about the object to be imaged and is the basis for reconstructing an image with a high quality.

In this embodiment, the primary beam image may be obtained by subtracting the scattering image from the pre-exposure image, that is, the primary beam image=the pre-exposure image−the scattering image.

In step S406, the first scatter kernel is updated based on a determination that the primary beam image fails to satisfy a convergence condition. Steps S402 to S406 are repeated until the primary beam image satisfies the convergence condition.

The convergence condition is, for example, that an error between the obtained primary beam image and a measured primary beam image is less than a predetermined error threshold. The measured primary beam image is a reference primary beam image actually generated by the detector and pre-stored for comparison with the obtained primary beam image. The measured primary beam image may be for example, generated by a detector using anti-scatter grids. The error may represent a residual value between the obtained primary beam image and the measured primary beam image or a gradient norm obtained by comparing the obtained primary beam image with the measured primary beam image. For example, the error may be a mean squared error between the obtained primary beam image and the measured primary beam image. The similarity between the two images can be evaluated by calculating the average of the squares of the differences between the pixel values corresponding to the two images, the smaller the average, the more similar the two images are. A mean squared error representing that the two images are sufficiently similar may be set as the predetermined error threshold. If the mean squared error between the obtained primary beam image and the measured primary beam image is less than the predetermined error threshold, it means the two images are sufficiently similar, and the convergence condition is satisfied.

If the primary beam image fails to satisfy the convergence condition, the first scatter kernel is updated until the primary beam image satisfies the convergence condition, thereby the scattering component in the pre-exposure image can be removed efficiently.

Figure 5:
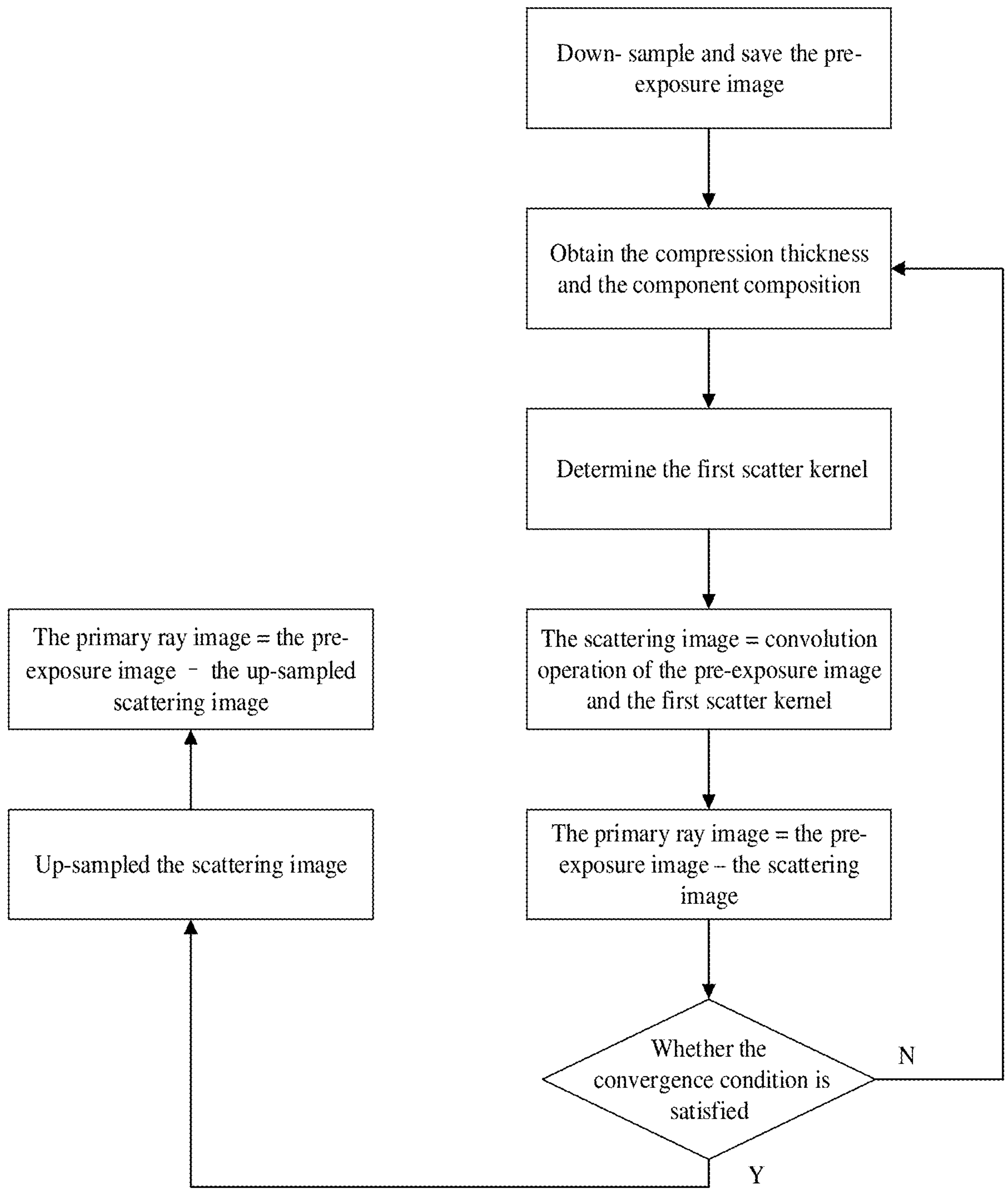
FIG. 5 is a flow diagram illustrating an overall process of removing scatter in a pre-exposure image according to an embodiment of the present disclosure.

FIG. 5 is a flow diagram illustrating an overall process of removing scatter in a pre-exposure image according to an embodiment of the present disclosure. As shown in FIG. 5, the pre-exposure image is down-sampled and saved. The compression thickness and the component composition of the phantom corresponding to the pre-exposure image is obtained. The corresponding first scatter kernel is determined based on the compression thickness and the component composition. The pre-exposure image is convolved with the first scatter kernel to obtain a scattering image. A primary beam image is obtained by subtracting the scattering image from the pre-exposure image. It is determined whether the primary beam image satisfies a convergence condition. If the primary beam image fails to satisfy a convergence condition, it is returned to the steps of obtaining the compression thickness and the component composition, until the primary beam image satisfies the convergence condition. When the primary beam image satisfies the convergence condition, the scattering image is up-sampled, and the primary beam image is obtained by subtracting the up-sampled scattering image from the pre-exposure image, to obtain the primary beam image, thereby performing the de-scattering processing on the pre-exposure image. In these processes, the pre-exposure image is down-sampled firstly, and then the scattering image is up-sampled. The down-sampling means the number of sampling points of the pre-exposure image is reduced, which can increase the sampling rate of the pre-exposure image. The up-sampling means the number of sampling points of the scattering image is increased so that the up-sampled scattering image has the same resolution as the pre-exposure image before being down-sampled.

Figures 6, 7, 8:
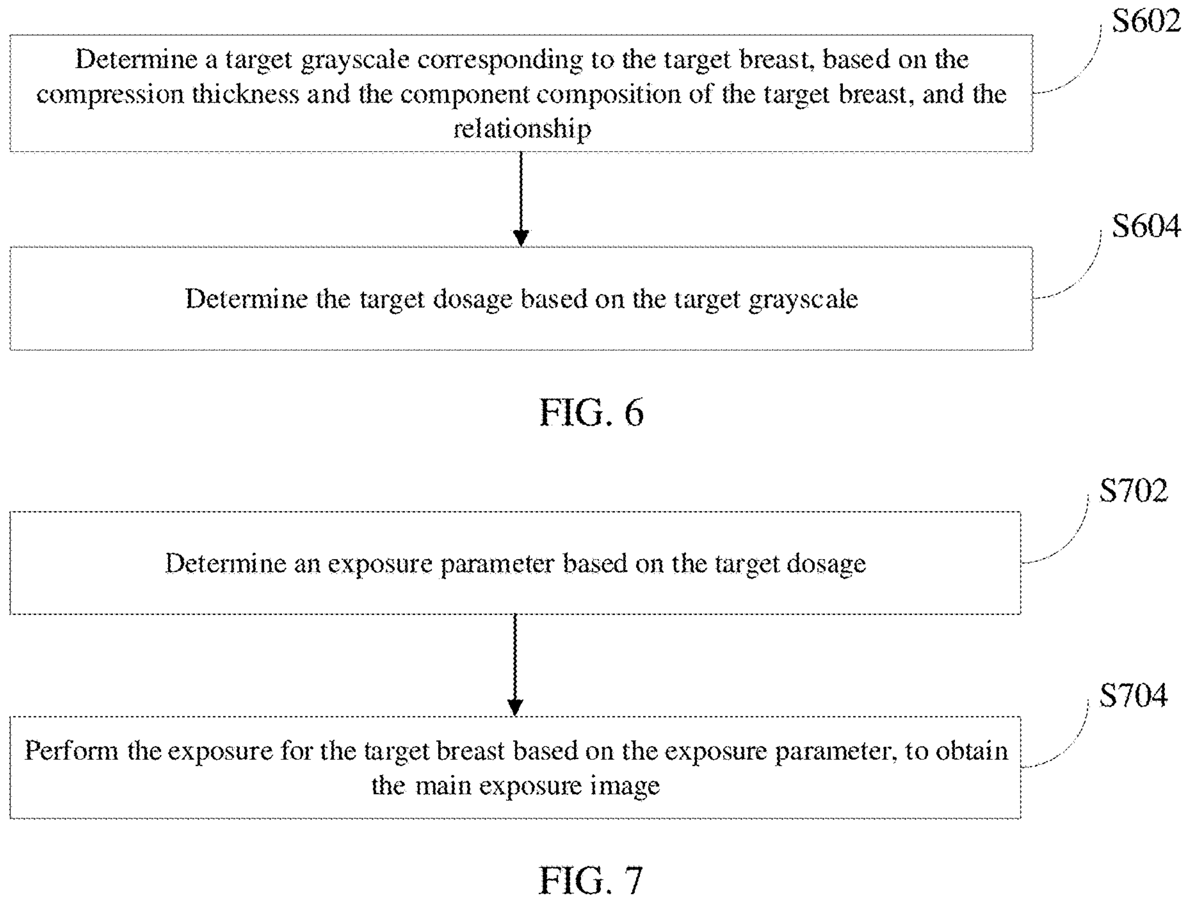
FIG. 6 is a flow diagram illustrating a process of determining a target dosage according to an embodiment of the present disclosure.
FIG. 7 is a flow diagram illustrating a process of main exposure according to an embodiment of the present disclosure.
FIG. 8 is a flow diagram illustrating a process of removing scatter in a main exposure image according to an embodiment of the present disclosure.

As shown in FIG. 6, the step S206 of determining the target dosage based on the compression thickness and the component composition of the target breast, and the relationship includes the following steps S602 and S604.

In step S602, a target grayscale for a target breast is determined, based on the compression thickness and the component composition of the target breast, and the relationship.

The relationship is, for example, a functional relationship among the target grayscale, the compression thickness and the component composition. The functional relationship may reflect how the target grayscale varies with the compression thickness or the component composition. The target grayscale can be determined based on the compression thickness and the component composition of the target breast.

In step S604, the target dosage is determined based on the target grayscale.

There exists a correspondence relationship between the target grayscale and the target dosage, so the target dosage can be determined based on the target grayscale. In this embodiment, given that there is the relationship among the target grayscale, the compression thickness, and component composition, the target dosage can be determined more accurately based on the compression thickness and the component composition of the target breast, and the relationship.

In other embodiments, the relationship among the target grayscale, the compression thickness and the component composition can be obtained via artificial intelligence (AI). Specifically, the relationship can be obtained via an artificial neural network. The compression thickness and the component composition of each the phantoms, and the grayscales of the pre-exposure images can be used to train the artificial neural network. When the compression thickness and the component composition of the target breast are used as inputs of the trained artificial neural network, the output of the trained artificial neural network is the target dosage for the target breast.

As shown in FIG. 7, the step S208 of performing exposure for the target breast based on the target dosage, to obtain the main exposure image includes the following steps S702 and S704.

In step S702, an exposure parameter is determined based on the target dosage.

In step S704, the main exposure is performed for the target breast based on the exposure parameter, to obtain the main exposure image.

In this embodiment, since the target dosage is obtained accurately, the exposure parameter can be obtained accurately. The exposure parameter includes, for example, a voltage or a current used when the ray source emits rays during the main exposure. The exposure parameter also includes, for example, a type of a target, or a type of a filter. After the exposure parameter is set, the ray source emits the ray of the target dosage, and the target breast is subjected to main exposure. As a result, the acquired main exposure image has the target grayscale.

Considering that the main exposure image may be still a mixed ray component image containing the primary beam component and the scattering component, the de-scattering processing may be performed on the main exposure image. As shown in FIG. 8, the method may further include the following steps S802 and S804.

In step S802, a second scatter kernel corresponding to the target breast is determined, based on the compression thickness and the component composition of the target breast.

In step S804, de-scattering iterative processing is performed on the main exposure image, based on the second scatter kernel.

It should be noted that the de-scattering processing in the steps S802 to S804 is the same as the de-scattering process for the pre-exposure image, and thus will not be described in detail.

It is considered that after the de-scattering iterative processing has been completed, the noise components brought by the low-frequency scattered rays may exist in the main exposure image. In some embodiments, the main exposure image after the de-scattering processing is denoised using a denoising and enhancement algorithm, to obtain an image of higher quality.

It should be understood that, although the various steps in the above-mentioned flow diagrams are displayed in sequence according to the indication of arrows, these steps are not necessarily executed in sequence according to the order indicated by the arrows. Unless there is a clear explanation in this disclosure, the execution of these steps is not strictly limited in order, and these steps can be executed in other orders. Moreover, at least a part of the steps in the above-mentioned flow diagrams may include multiple steps or multiple stages, and these steps or stages are not necessarily executed at the same time, but can be executed at different times, and the execution order of these steps or stages is not necessarily to be carried out in sequence, but can be executed in turn or alternately with other steps or at least a part of the steps or stages in other steps.

Referring back to FIG. 1, another aspect of the present disclosure provides a mammography system 100. The mammography system 100 includes a scanning device 110 and a processing device 140. The scanning device 110 is configured to: generate pre-exposure images respectively corresponding to a plurality of phantoms by performing pre-exposure for each of the plurality of phantoms with a respective predetermined dosage; and generate a main exposure image by performing exposure for a target breast based on a target dosage. The processing device 140 is configured to: acquire the pre-exposure images from the scanning device; determine a relationship among a target grayscale, the compression thickness and the component composition by performing de-scattering processing on each pre-exposure image based on the compression thickness and the component composition of the phantom corresponding to the pre-exposure image; determine a target dosage for a target breast based on a compression thickness and a component composition of the target breast, and the relationship; and acquire the main exposure image from the scanning device.

In some embodiments, performing de-scattering processing on each pre-exposure image based on the compression thickness and the component composition of the phantom corresponding to the pre-exposure image includes: determining a first scatter kernel corresponding to the phantom, based on the compression thickness and the component composition of the phantom; and performing de-scattering iterative processing on the pre-exposure image, based on the first scatter kernel corresponding to the phantom.

In some embodiments, performing de-scattering iterative processing on the pre-exposure image, based on the first scatter kernel corresponding to the phantom, includes: obtaining a scattering image corresponding to the pre-exposure image by performing a convolution operation on the pre-exposure image and the first scatter kernel; obtaining a primary beam image corresponding to the phantom, based on the pre-exposure image and the scattering image; and updating the first scatter kernel based on a determination that the primary beam image fails to satisfy a convergence condition, until the primary beam image satisfies the convergence condition.

In some embodiments, determining the target dosage for the target breast based on the compression thickness and the component composition of the target breast, and the relationship, includes: determining a target grayscale corresponding to the target breast, based on the compression thickness and the component composition of the target breast, and the relationship; and determining the target dosage based on the target grayscale.

In some embodiments, the processing device 140 is further configured to: determine an exposure parameter based on the target dosage; and transmit the exposure parameter to the scanning device.

In some embodiments, the processing device 140 is further configured to: determining a second scatter kernel corresponding to the target breast, based on the compression thickness and the component composition of the target breast; and performing de-scattering iterative processing on the main exposure image, based on the second scatter kernel.

For the specific definition of the functions or processes implemented by the scanning device or the processing device, please refer to the definition of the method described above, which will not be repeated here.

A further aspect of the present disclosure provides a computer apparatus. The computer apparatus may be a server. FIG. 9 shows an internal configuration of the computer apparatus. The computer apparatus includes a processor, a memory, and a network interface connected via a system bus. The processor of the computer apparatus is used to provide computing and control capabilities. The memory of the computer apparatus includes a non-volatile storage medium and an internal memory. The non-volatile storage medium stores an operating system, a computer program, and a database. The internal memory provides an environment for the operation of the operating system and the computer program in the non-volatile storage medium. The database of the computer apparatus is used to store motion detection data. The network interface of the computer apparatus is used to communicate with an external terminal via a network connection. When the computer program is executed by the processor, the processor is caused to implement steps of: obtaining pre-exposure images respectively corresponding to a plurality of phantoms, each phantom having its respective compression thickness and component composition by performing pre-exposure for each of the plurality of phantoms with a respective predetermined dosage; determining a relationship among a target grayscale, the compression thickness and the component composition by performing de-scattering processing on each pre-exposure image based on the compression thickness and the component composition of the phantom corresponding to the pre-exposure image; determining a target dosage for a target breast based on a compression thickness and a component composition of the target breast, and the relationship; and acquiring a main exposure image by performing exposure for the target breast based on the target dosage.

In some embodiments, performing de-scattering processing on each pre-exposure image based on the compression thickness and the component composition of the phantom corresponding to the pre-exposure image includes: determining a first scatter kernel corresponding to the phantom, based on the compression thickness and the component composition of the phantom; and performing de-scattering iterative processing on the pre-exposure image, based on the first scatter kernel corresponding to the phantom.

In some embodiments, performing de-scattering iterative processing on the pre-exposure image, based on the first scatter kernel corresponding to the phantom, includes: obtaining a scattering image corresponding to the pre-exposure image by performing a convolution operation on the pre-exposure image and the first scatter kernel; obtaining a primary beam image corresponding to the phantom, based on the pre-exposure image and the scattering image; and updating the first scatter kernel based on a determination that the primary beam image fails to satisfy a convergence condition, until the primary beam image satisfies the convergence condition.

In some embodiments, determining the target dosage for the target breast based on the compression thickness and the component composition of the target breast, and the relationship, includes: determining a target grayscale corresponding to the target breast, based on the compression thickness and the component composition of the target breast, and the relationship; and determining the target dosage based on the target grayscale.

In some embodiments, performing exposure for the target breast based on the target dosage, to obtain the main exposure image, includes: determining an exposure parameter based on the target dosage; and performing the exposure for the target breast based on the exposure parameter, to obtain the main exposure image.

In some embodiments, when the computer program is executed by the processor, the processor is caused to implement steps of: determining a second scatter kernel corresponding to the target breast, based on the compression thickness and the component composition of the target breast; and performing de-scattering iterative processing on the main exposure image, based on the second scatter kernel.

In some embodiments, when the computer program is executed by the processor, the processor is caused to implement a step of denoising the main exposure image after the de-scattering iterative processing has been completed.

Those of ordinary skill in the art will understand that FIG. 9 is merely a block diagram of a partial configuration related to the solution of the present disclosure, and does not constitute a limitation on the computer apparatus to which the solution of the present disclosure is applied. The computer apparatus may include more or fewer components than shown in the figure, combine certain components, or have a different arrangement of components.

A further aspect of the present disclosure provides a computer-readable storage medium, on which a computer program is stored. When the computer program is executed by a processor, the steps of any method described above are implemented.

Those of ordinary skill in the art can understand that all or part of the processes in the above-mentioned embodiments of the method can be completed by instructing the relevant hardware through a computer program, and the computer program can be stored in a non-volatile computer-readable storage medium. When the computer program is executed, it can include the processes of the embodiments of the above-mentioned methods. Any reference to memory, storage, database, or other media used in the embodiments provided in this disclosure may include at least one non-volatile memory or volatile memory. The non-volatile memory may include read-only memory (ROM), tape, floppy disk, flash memory or optical memory, etc. The volatile memory may include random access memory (RAM) or external cache memory. As an illustration and not a limitation, RAM can be in various forms, such as static random access memory (SRAM) or dynamic random access memory (DRAM).

Although various illustrative embodiments are described above, any of a number of changes may be made to various embodiments without departing from the scope of the present disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the present disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for imaging at least part of a breast with a mammography system, the method comprising:

obtaining pre-exposure images respectively corresponding to a plurality of phantoms by performing pre-exposure for each of the plurality of phantoms with a respective predetermined dosage, each phantom having its respective compression thickness and component composition;

determining a relationship among a target grayscale, the compression thickness, and the component composition by performing de-scattering processing on each pre-exposure image based on the compression thickness and the component composition of the phantom corresponding to the pre-exposure image;

determining a target dosage for a target breast based on a compression thickness of the target breast, a component composition of the target breast, and the relationship; and acquiring a main exposure image by performing exposure for the target breast based on the target dosage, the main exposure image having the target grayscale.

2. The method of claim 1, wherein performing de-scattering processing on each pre-exposure image based on the compression thickness and the component composition of the phantom corresponding to the pre-exposure image comprises:

determining a first scatter kernel corresponding to the phantom, based on the compression thickness and the component composition of the phantom; and performing de-scattering iterative processing on the pre-exposure image, based on the first scatter kernel corresponding to the phantom.

3. The method of claim 2, wherein performing de-scattering iterative processing on the pre-exposure image, based on the first scatter kernel corresponding to the phantom, comprises:

obtaining a scattering image corresponding to the pre-exposure image by performing a convolution operation on the pre-exposure image and the first scatter kernel;

obtaining a primary beam image corresponding to the phantom, based on the pre-exposure image and the scattering image; and updating the first scatter kernel based on a determination that the primary beam image fails to satisfy a convergence condition, until the primary beam image satisfies the convergence condition.

4. The method of claim 3, wherein obtaining a primary beam image corresponding to the phantom, based on the pre-exposure image and the scattering image, comprises:

subtracting the scattering image from the pre-exposure image to obtain the primary beam image corresponding to the phantom.

5. The method of claim 3, wherein the convergence condition is that an error between the obtained primary beam image and a measured primary beam image is less than a predetermined error threshold.

6. The method of claim 1, wherein determining the target dosage for the target breast based on the compression thickness and the component composition of the target breast, and the relationship, comprises:

determining a target grayscale corresponding to the target breast, based on the compression thickness and the component composition of the target breast, and the relationship; and determining the target dosage based on the target grayscale.

7. The method of claim 1, wherein acquiring the main exposure image by performing exposure for the target breast based on the target dosage, comprises:

determining an exposure parameter based on the target dosage; and performing the exposure for the target breast based on the exposure parameter, to obtain the main exposure image.

8. The method of claim 1, further comprising:

determining a second scatter kernel corresponding to the target breast, based on the compression thickness and the component composition of the target breast; and performing de-scattering iterative processing on the main exposure image, based on the second scatter kernel.

9. The method of claim 8, further comprising:

denoising the main exposure image after the de-scattering iterative processing has been completed.

10. A mammography system, comprising:

a scanning device configured to:

generate pre-exposure images respectively corresponding to a plurality of phantoms by performing pre-exposure for each of the plurality of phantoms with a respective predetermined dosage, each phantom having its respective compression thickness and component composition; and generate a main exposure image by performing exposure for a target breast based on a target dosage; and a processing device configured to:

acquire the pre-exposure images from the scanning device;

determine a relationship among a target grayscale, the compression thickness and the component composition by performing de-scattering processing on each pre-exposure image based on the compression thickness and the component composition of the phantom corresponding to the pre-exposure image;

determine a target dosage for a target breast based on a compression thickness and a component composition of the target breast, and the relationship; and acquire the main exposure image from the scanning device.

11. The mammography system of claim 10, wherein performing de-scattering processing on each pre-exposure image based on the compression thickness and the component composition of the phantom corresponding to the pre-exposure image comprises:

determining a first scatter kernel corresponding to the phantom, based on the compression thickness and the component composition of the phantom; and performing de-scattering iterative processing on the pre-exposure image, based on the first scatter kernel corresponding to the phantom.

12. The mammography system of claim 11, wherein performing de-scattering iterative processing on the pre-exposure image, based on the first scatter kernel corresponding to the phantom, comprises:

obtaining a scattering image corresponding to the pre-exposure image by performing a convolution operation on the pre-exposure image and the first scatter kernel;

obtaining a primary beam image corresponding to the phantom, based on the pre-exposure image and the scattering image; and updating the first scatter kernel based on a determination that the primary beam image fails to satisfy a convergence condition, until the primary beam image satisfies the convergence condition.

13. The mammography system of claim 10, wherein determining the target dosage for the target breast based on the compression thickness and the component composition of the target breast, and the relationship, comprises:

determining a target grayscale corresponding to the target breast, based on the compression thickness and the component composition of the target breast, and the relationship; and determining the target dosage based on the target grayscale.

14. The mammography system of claim 10, wherein the processing device is further configured to:

determine an exposure parameter based on the target dosage; and transmit the exposure parameter to the scanning device.

15. The mammography system of claim 10, wherein the processing device is further configured to:

determine a second scatter kernel corresponding to the target breast, based on the compression thickness and the component composition of the target breast; and perform de-scattering iterative processing on the main exposure image, based on the second scatter kernel.

16. A method for imaging at least part of a breast with a mammography system, the method comprising:

obtaining a relationship among a target grayscale, a compression thickness, and a component composition;

determining a target dosage for a target breast based on the relationship, a compression thickness of the target breast, and a component composition of the target breast; and performing exposure for the target breast based on the target dosage.

17. The method of claim 16, wherein the relationship is obtained by:

obtaining pre-exposure images respectively corresponding to a plurality of phantoms by performing pre-exposure for each of the plurality of phantoms with a respective predetermined dosage, each phantom having its respective compression thickness and component composition; and determining the relationship among the target grayscale, the compression thickness and the component composition by performing de-scattering processing on each pre-exposure image based on the compression thickness and the component composition of the phantom corresponding to the pre-exposure image.

18. The method of claim 16, wherein the relationship is obtained via artificial intelligence (AI).

19. The method of claim 17, wherein performing de-scattering processing on each pre-exposure image based on the compression thickness and the component composition of the phantom corresponding to the pre-exposure image comprises:

determining a first scatter kernel corresponding to the phantom, based on the compression thickness and the component composition of the phantom; and performing de-scattering iterative processing on the pre-exposure image, based on the first scatter kernel corresponding to the phantom.

20. The method of claim 19, wherein performing de-scattering iterative processing on the pre-exposure image, based on the first scatter kernel corresponding to the phantom, comprises:

obtaining a scattering image corresponding to the pre-exposure image by performing a convolution operation on the pre-exposure image and the first scatter kernel;

obtaining a primary beam image corresponding to the phantom, based on the pre-exposure image and the scattering image; and updating the first scatter kernel based on a determination that the primary beam image fails to satisfy a convergence condition, until the primary beam image satisfies the convergence condition.

* * * * *